United States Patent [19]
Collins

[11] Patent Number: 6,054,182
[45] Date of Patent: Apr. 25, 2000

[54] METHOD FOR TREATING GARMENTS WITH INSECT REPELLENT

[76] Inventor: Daniel R. Collins, P.O. Box 344, Sagamore, Mass. 02561

[21] Appl. No.: 09/056,800

[22] Filed: Apr. 8, 1998

[51] Int. Cl.[7] .................................................. B05D 3/12
[52] U.S. Cl. ......................... 427/242; 427/255.6; 239/36
[58] Field of Search ................................. 427/242, 255.6; 239/6, 36, 60, 54, 55

[56] References Cited

U.S. PATENT DOCUMENTS

| | | | |
|---|---|---|---|
| 3,686,025 | 8/1972 | Morton | 117/140 R |
| 4,649,046 | 3/1987 | Kross | 424/76 |
| 4,804,683 | 2/1989 | Steltenkamp | 514/629 |
| 4,959,208 | 9/1990 | Chakrabarti et al. | 424/78 |
| 5,006,562 | 4/1991 | Steltenkamp | 514/625 |
| 5,015,665 | 5/1991 | Steltenkamp | 514/625 |
| 5,035,886 | 7/1991 | Chakrabarti et al. | 424/78 |
| 5,071,645 | 12/1991 | Johnson et al. | 424/486 |
| 5,182,304 | 1/1993 | Steltenkamp | 514/625 |
| 5,182,305 | 1/1993 | Steltenkamp | 514/629 |
| 5,238,682 | 8/1993 | Akasaka et al. | 424/409 |
| 5,258,408 | 11/1993 | Steltenkamp | 514/625 |
| 5,391,578 | 2/1995 | Steltenkamp | 514/625 |
| 5,434,189 | 7/1995 | Steltenkamp | 514/625 |
| 5,434,190 | 7/1995 | Steltenkamp | 514/629 |
| 5,455,043 | 10/1995 | Fischel-Ghodsian | 424/448 |
| 5,547,476 | 8/1996 | Siklosi et al. | 8/142 |

*Primary Examiner*—Shrive Beck
*Assistant Examiner*—Kirsten A. Crockford
*Attorney, Agent, or Firm*—Thomas A. Kahrl

[57] ABSTRACT

A method of delivery of insect repellent which incorporates a delivery device which provides for release of insect repellent to fabrics within an automatic laundry dryer at dryer operating temperatures for treating garments for the purpose of repelling insects and which controls the amount and toxicity of a repellent applied directly to garments, particularly children's garments, and which eliminates the direct application of toxic repellent to the skin of a user for use in controlling the spread of Lyme Disease.

3 Claims, 2 Drawing Sheets

METHOD FOR TREATING GARMENTS WITH INSECT REPELLENT

BACKGROUND OF THE INVENTION

1. Field of the Invention (Technical Field)

The present invention relates to an active agent delivery device for use in applying insect repellent to clothes as part of the drying cycle of a clothes dryer. In particular the invention is directed to a delivery device which provides for release of insect repellent to fabrics within an automatic laundry dryer at dryer operating temperatures for treating children's garments for the purpose of repelling deer ticks to prevent Lyme Disease.

2. Prior Art Delivery Methods

Eradicate With Pump Gun

Many types of insects are classified as pests, and many efforts have been made to eradicate or, at the very least, control them. An early application was the product FLIT, developed for the purpose of ridding an area of pests, the trademark advertising slogan showing that once an offensive insect was encountered, "Quick Henry The Flit" was applied by means of a pump gun with spray device (see FIGS. 1–3). Notwithstanding the development of effective poisons, which have been substantially effective in controlling insects such as mosquitoes, it has been found that many poisons, a case in point being the chemical commonly known as DDT, have undesirable effects on human and other animal life and therefore uses of many are now regulated or forbidden. See Rachel Carson, Silent Spring.

Freon Spray Delivery

More recently efforts have been directed to controlling offensive insects, rather than to eradicating them. Products such as 6–12 have been marketed as an aerosol, replacing the pump gun. This delivery was very popular, so much so that we are now faced with the threat of global warming. For environmental and health reasons the aerosol spray has proved more of a threat than a solution.

Toxicity

Often, an effective repellent is the only feasible means to prevent the mosquito bites which for many produce an allergic reaction. Some such repellents are of low toxicity, such that they may be applied to the human body and onto pets, zoo animals and livestock. However, some other repellent materials are toxic and others are foul smelling and discoloring, which adverse properties can seriously limit their utility. Many of the useful insect repellents reported in the literature are tertiary amides and of these the one heretofore regarded as the most effective all-purpose insect repellent is N,N-diethyl-m-toluamide, which is often referred to as "DEET". It is effective in repelling mosquitoes, black flies, carpenter ants and deer ticks. In view of the relatively small number of useful insect repellents known, many of which are toxic when applied to the skin of children, efforts continue to be made to discover delivery devices for applying such repellents to garments, particularly children's garments. Desirably, such compounds also would be of improved physical characteristics, such as even better aroma, desirable volatility, non-staining character, even lower toxicity, improved stability, greater substantivity to substrates, and repellency against a broader group of insect types.

Lyme Disease

Whereas many insects are considered a nuisance, others have proved to be a significant health threat, particularly to children. Lyme disease is one such threat. The following are excerpts explaining Lyme disease and some of the difficulties it poses.

1) AMERICAN ACADEMY OF PEDIATRICS: Lyme Disease Fact Sheet

What is Lyme disease? Lyme disease is a bacterial infection caused by the spirochete *Borrelia burgdorferi*.

Early symptoms: The Lyme disease rash, called erythema migrans, may start out as a small red spot at the site of the bite. This spot typically expands after several days. The rash may be circular or oval shaped with a partial central clear area. More sports can develop after the first one. The rash is sometimes described as a "target" or "bull's eye" but many Lyme disease rashes do not follow this pattern. The rash is often accompanied by fever, headache, mild neck stiffness and flu-like symptoms that come and go.

Later symptoms: Weeks to months later, children with untreated Lyme disease may develop arthritis, neurologic problems, or meningitis.

How is Lyme disease spread? Lyme disease is transmitted to humans by certain infected black-legged ticks (sometimes called deer or bear ticks). Lyme disease is NOT spread by the common American dog tick.

Children can contract the disease when they are bitten by black-legged ticks that have been feeding on infected animals.

Most cases of Lyme disease occur in warm months. The incubation period is 3–31 days.

What can parents and child care providers do? Avoid black-legged tick habitats (tall brassy areas, bushes, wooded areas) if possible. If on a hike, walk in the center of the trail to avoid brushing against trees and bushes.

Dress children appropriately if entering a tick-infested area. Have children wear a hat, light colored clothing, long sleeves, long pants tucked into socks, and closed shoes or sneakers.

Permethrin can be sprayed on clothing to prevent tick attachment. If you use DEET tick repellent on exposed skin or clothing, apply it sparingly because seizures have been associated with its use in children. Apply spray repellents out-of-doors. Do not apply DEET to children's hands that they may put into their mouths and eyes. Once indoors, remove DEET with soap and water. Remove and launder clothes.

Check children's skin and scalp daily for ticks. If you discover a tick attached to a child's skin, follow the Infant & Child First Aid guidelines of the American Red Cross. Wearing gloves, grasp the tick with tweezers as close to the child's skin as possible. Pull slowly to avoid breaking the tick. If you cannot remove the tick, or if parts of the tick remain in the skin, get medical help. If you do not have tweezers, use a glove, plastic wrap or a piece of paper to protect your fingers. If you must use your bare fingers, wash you hands immediately afterward. Wash the bite area with soap and water. If the child feels ill, get medical help without delay. Be sure to tell the parents that the child has had a tick bite.

2) AMERICAN FORCES PRESS SERVICE: Protecting Yourself From Lyme Disease

People can pick up ticks during walks in parks or the woods, or while hiking and camping. Children are especially susceptible because they run around in tall grass, play in wooded areas and roll on the ground, researchers have noted.

The individual risk of getting Lyme disease is reasonably small. Only about 12 to 15 percent of ticks actually carry the disease. Experts said removing ticks from the body quickly may prevent a person from contracting Lyme disease. Ticks generally must feed on a person for 24 to 48 hours before the person becomes infected.

Lyme disease experts warn field troops not to wear tick and flea collars meant for pets. Cats and dogs don't sweat, but people do, and harmful chemicals can get into the human body through sweat glands.

Named after Lyme, Conn., where it surfaced in 1975, Lyme disease has become one of the fastest-growing vector-borne diseases in the United States. The highest incidence occurs in the Northeast from Massachusetts to Maryland and in Wisconsin, Minnesota, California and Oregon. A vector is a host that passes the disease germ—the tick, in the case. Researchers at the Armed Forces Pest Management Board note that all military recruit training areas are infested with ticks.

The best way to avoid Lyme disease is to stay away from places where ticks live—tall grass and weeds, scrubby areas, woods and leaf litter. Another good idea: Check children and pets after they've played outside.

Service members can use a two-part DoD chemical repellent system consisting of a permethrin-based spray for clothing and DEET-based lotion for exposed skin. The repellents should be coupled with proper wearing of the uniform.

If you can't avoid tick-infested areas, CDC experts suggest you wear a long-sleeved shirt and long pants, tuck pant legs into socks or boots, tuck shirt into pants, tape area where pants and socks meet to keep ticks out and wear light-colored clothing so ticks can be seen easily.

After being outdoors:

Promptly remove and wash clothing;

Inspect your body carefully and remove attached ticks with tweezers, grasping as close to the head as possible and gently tugging the tick free without crushing its body. Squeezing the tick's body may force infected fluid into the wound;

Place tick in sealed container for examination by a local health department; and Wash the wound and apply an antiseptic.

3) UNIVERSITY OF PENN: Watching out for Lyme Disease

These precautions can help reduce the risk: (a) wear light-colored clothing so ticks can be easily spotted, (b) wear long-sleeved shirts with tight cuffs, (c) wear long pants tied at the ankle or stuffed into socks, (d) wear light-colored socks and closed shoes, (e) use insect repellent containing DEET on clothing (especially shoe tops and pant legs), (f) put tick repellent collars on pets and (g) check yourself, your children, and your pets for ticks before coming indoors.

4) UNIVERSITY OF MISSOURI: Ways to Reduce the Risk of Lyme Disease:

The best prevention is to use an insect repellent with the ingredient, DEET (a concentration of 35% to 55% is recommended for best protection).

Accordingly, it is desirable to provide for a new and improved method of protecting against insects, particularly carriers of Lyme Disease, to provide for a method of delivery of insect repellent which controls the amount and toxicity of a repellent applied directly to garments, particularly childrens garments, and which eliminates the direct application of toxic repellent to the skin of a user which overcomes at least some of the disadvantages of prior art.

SUMMARY OF THE INVENTION

The present invention is directed to providing an improved method of delivery of insect repellent. In particular it is directed to a method of delivery of insect repellent which controls the amount and toxicity of a repellent applied directly to garments, particularly children's garments, and which eliminates the direct application of toxic repellent to the skin of a user for use in controlling the spread of Lyme Disease.

The present invention is directed to an active agent delivery device for use in applying insect repellent to clothes as part of the drying cycle of a clothes dryer. In particular the invention is directed to a delivery device which provides for release of insect repellent to fabrics within an automatic laundry dryer at dryer operating temperatures for treating children's garments for the purpose of repelling deer ticks to prevent Lyme Disease.

The present invention is particularly directed to providing an article of manufacture adapted for use to impart insect repellent to fabrics in an automatic laundry dryer comprising: a dispensing means which provides for release of an effective amount of said repellent to fabrics in the dryer at automatic dryer operating temperatures, i.e. 35° C. to 115° C.

The invention also encompasses a method for imparting an insect repellent by means of an active agent delivery device to fabrics in an automatic clothes dryer comprising tumbling said fabrics under heat in a clothes dryer. In the present invention said active agent delivery device is based on microporous material characterized by a matrix of finely-divided particulate siliceous filler.

Accordingly, one embodiment of the invention is an active agent delivery device which releases active agent in a dryer environment comprising (1) microporous material comprising (a) a matrix, (b) finely divided particulate substantially water-insoluble filler, and (c) having pores communicating throughout the microporous material, and (2) a releasable active agent associated with the filler.

Another embodiment of the invention is a process for producing an active agent delivery device which releases active agent in a dryer environment comprising (1) microporous material comprising (a) a matrix and (b) finely divided particulate substantially water-insoluble filler, and (c) having pores communicating throughout the microporous material, and (2) a releasable active agent associated with the filler.

The releasable active agent comprises DEET. DEET is a substance or mixture of substances which, when delivered by the delivery device to the surrounding environment is useful releasing insecticides, for one or more purposes in the surrounding environment such as repelling deer ticks from a garment.

It is a general object of the present invention to provide an improved method of delivery of insect repellent.

More particularly, it is an object of the invention to provide a method for imparting an insect repellent by means of an active agent delivery device to fabrics in an automatic clothes dryer comprising tumbling said fabrics under heat in a clothes dryer.

Another object of the invention is to provide a method of delivery of insect repellent which controls the amount and toxicity of a repellent applied directly to garments, particularly children's garment.

A further object is to provide improved method of delivery of insect repellent which eliminates the direct application of toxic repellent to the skin of a user for use in controlling the spread of Lyme Disease.

Yet another object of the invention is to provide an article of manufacture adapted for use to impart insect repellent to fabrics in an automatic laundry dryer comprising: a dispensing means which provides for release of an effective amount of said repellent to fabrics in the dryer at automatic dryer operating temperatures, i.e., 35° C. to 115° C.

These and other objects, advantages, and features of the invention will be apparent from the following description of preferred embodiments considered along with the accompanying drawings. The invention will be described for the purposes of illustration only in connection with certain embodiments; however, it is recognized that those persons skilled in the art may make various changes, modifications, improvements and additions on the illustrated embodiments all without departing from the spirit and scope of the invention.

BRIEF DESCRIPTION OF THE DRAWINGS

The accompanying drawings, which are incorporated into and form a part of the specification, illustrate several embodiments of the present invention and together with the description serve to explain the principals of the invention. The drawings are only for the purpose of illustrating a preferred embodiment of the invention and are not construed as limiting the invention.

Figure 1:
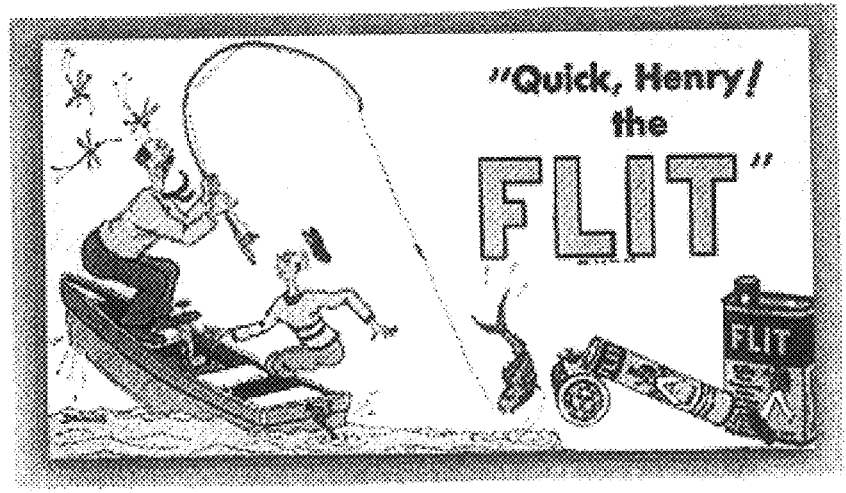
FIG. 1 is a graphic illustration of prior art depicting a 1930 advertisement drawn by Dr. Seuss showing insects attacking fishermen in a boat and the product Flit Bug Spray.
Figure 2:
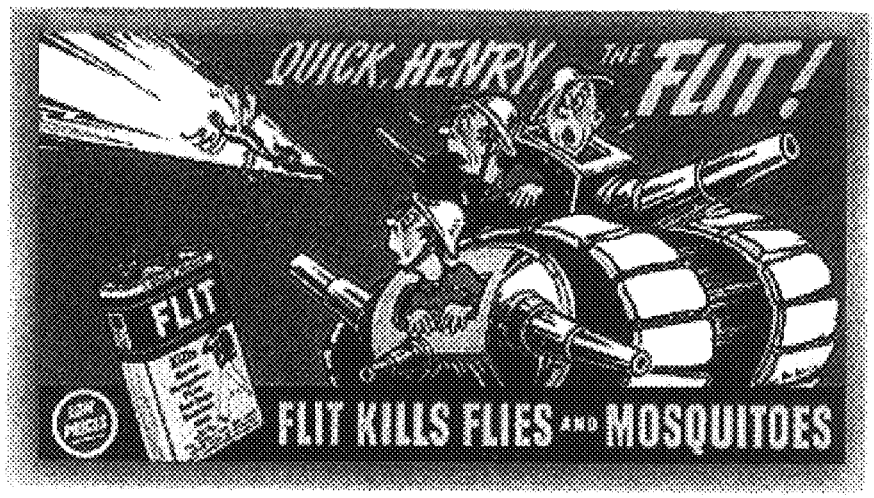
FIG. 2 is a graphic illustration of prior art depicting an insect attacking soldiers in a tank and the product Flit, advertised as killing flies and mosquitoes.
Figure 3:
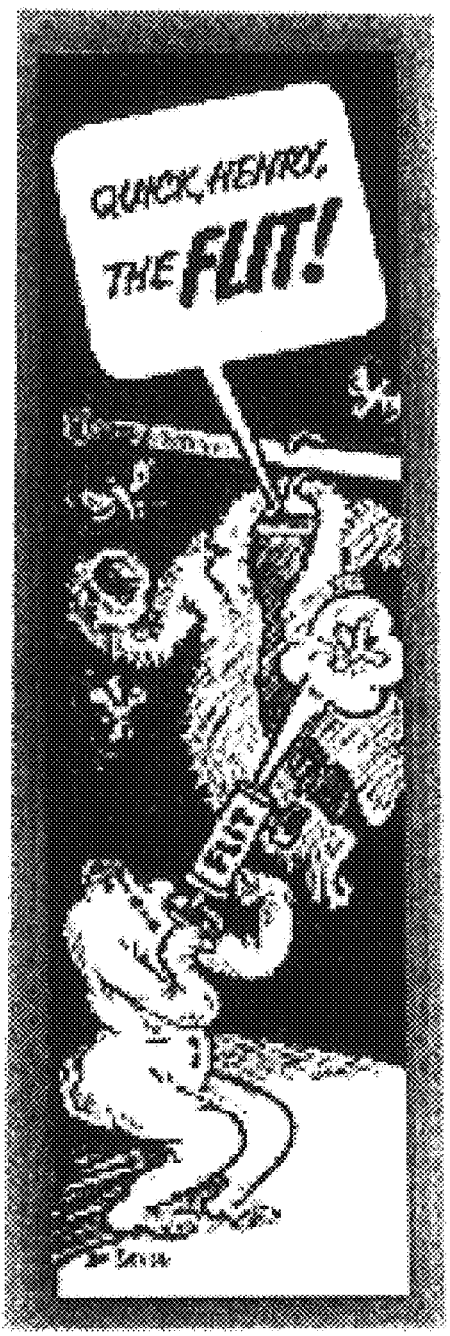
FIG. 3 is a graphic illustration of prior art depicting a 1930's advertisement for Flit, showing the product being sprayed at a garment that has moths around it.

The invention will be described for the purposes of illustration only in connection with certain embodiments; however, it is recognized that those persons skilled in the art may make various changes, modifications, improvements and additions on the illustrated embodiments all without departing from the spirit and scope of the invention.

DETAILED DESCRIPTION OF THE PREFERRED EMBODIMENT

The preferred embodiment is directed to the inventive combination of an improved method of delivery of insect repellent. In particular it is directed to a method of delivery of insect repellent which controls the amount and toxicity of a repellent applied directly to garments, particularly children's garments and which eliminates the direct application of toxic repellent to the skin of a user for use in controlling the spread of Lyme Disease.

The present invention includes an article of manufacture, typically a matrix, placed in a bag together with garments adapted for use to impart insect repellent to fabrics in an automatic laundry dryer comprising: a dispensing means in the matrix which provides to release of an effective amount of said repellent to fabrics in the dryer at automatic dryer operating temperatures, i.e., 35° C. to 115° C.

The invention also encompasses a method for imparting an insect repellent by means of an active agent delivery device to fabrics in an automatic clothes dryer comprising tumbling said fabrics under heat in a clothes dryer. In the present invention said active agent delivery device is based on microporous material characterized by a matrix of finely-divided particulate siliceous filler. In the preferred embodiment of the invention an active agent delivery device which releases active agent in a dryer environment comprising (1) microporous material comprising (a) a matrix, (b) finely divided particulate substantially water-insoluble filler, and (c) having pores communicating throughout the microporous material, and (2) a releasable active agent associated with the filler.

Another embodiment of the invention is a process for producing an active agent delivery device which releases active agent in a dryer environment comprising (1) microporous material comprising (a) a matrix, (b) finely divided particulate substantially water-insoluble filler, and (c) having pores communicating throughout the microporous material, and (2) a releasable active agent associated with the filler. The releasable active agent comprises DEET, a substance or mixture of substances which, when delivered by the delivery device to the surrounding environment is useful releasing insecticides, for one or more purposes in the surrounding environment.

The invention provides a method for imparting an insect repellent by means of an active agent delivery device to fabrics in an automatic clothes dryer comprising tumbling said fabrics under heat in a clothes dryer which controls the amount and toxicity of a repellent applied directly to garments, particularly children's garment. This method of delivery of insect repellent which eliminates the direct application of toxic repellent to the skin of a user is for use in controlling the spread of Lyme Disease. Also, applying the repellent to clothing may prevent insects from landing on the clothing and its wearer, and from stinging or biting the wearer.

While different application rates this invention are desirable used for effective repelling of different insects from garment surfaces under different conditions, it is generally considered that insect repellent effects are obtainable at surface concentrations of the active ingredient in the range of 0.002 to 100 g./sq.m. For economic reasons and for effectiveness against more insects there will normally be applied 0.1 or 0.2 to 10 g./sq.m., preferably 0.5 to 2 g./sq.m., e.g. 1 g/sq.m. Higher application rates, such as 10 to 100 g/sq.m., can be used against other insects, such as mosquitoes.

What is claimed is:

1. A method of delivery of insect repellent comprising a delivery device which provides for release of insect repellent to garments agitated within an automatic laundry dryer at dryer operating temperatures for the purpose of repelling ticks comprising the steps of;
    a) providing an automatic laundry dryer;
    b) providing garments to be treated;
    c) providing a single purpose active insect agent delivery device comprising (1) microporous material comprising (a) a matrix, (b) finely divided particulate substantially water-insoluble filler, and (c) having pores communicating throughout the microporous material, and (2) a releasable active agent associated with the filler, said active agent consisting of tick repellent;
    d) agitating said garments in combination with said delivery device in said automatic dryer for a controlled amount of time, to treat the garments with said tick repellent in a controlled manner thus applying tick repellent to said garments for the purpose of protecting garment users from being bitten by ticks.

2. The method of claim 1 wherein the automatic dryer operating temperatures are between 35° C. to 115° C.

3. The method of claim 1 wherein the tick repellent is DEET.

* * * * *